United States Patent [19]

Weinstein

[11] Patent Number: 5,242,418

[45] Date of Patent: Sep. 7, 1993

[54] PROTECTIVE MEANS FOR A NEEDLE OR SIMILAR CANNULA MEDICAL DEVICE

[76] Inventor: James D. Weinstein, 1109 Woodland Dr., Bridgeport, W. Va. 26330

[21] Appl. No.: 888,060

[22] Filed: May 22, 1992

[51] Int. Cl.$^5$ ............................................. A61M 5/32
[52] U.S. Cl. ................................. 604/192; 604/263
[58] Field of Search ............... 604/192, 198, 187, 110, 604/263

[56] References Cited

U.S. PATENT DOCUMENTS 4,139,009 2/1979 Alvarez .............................. 604/198

Primary Examiner—John D. Yasko
Attorney, Agent, or Firm—Cindrich & Titus

[57] ABSTRACT

A protective sheath for a cannula which has distal end for percutaneous insertion and a proximate end having a hub or like assembly. The protective sheath comprises an elongated, flexible tubular member which slidably fits over the cannula. The tubular member has a distal end which is disposed over the distal end of the cannula and is compressibly retractable therefrom. The distal end of the tubular member has an opening through which the cannula may pass so as to expose the distal end of the cannula during insertion thereof, but when the cannula is withdrawn, the distal end of the sheath extends over and covers the distal end of the cannula.

12 Claims, 4 Drawing Sheets

PROTECTIVE MEANS FOR A NEEDLE OR SIMILAR CANNULA MEDICAL DEVICE

FIELD OF INVENTION

The present invention relates to a protective means for cannula used as needles, syringes, catheters and like medical appliances and, in particular, to a means for protecting against accidental contact with a sharp pointed cannula.

BACKGROUND OF THE INVENTION

Recently a great deal of concern has been expressed over the accidental or inadvertent contact with sharp pointed cannula used in syringes, catheters and the like causing the spread of various diseases. In addition to hepatitis, acquired immune deficiency syndrome has led to the design of disposable syringes having retractable cannulas or other protective means to prevent the inadvertent piercing of the skin of a third party after an injection or the removal of a catheter. For example, see U.S. Pat. Nos. 4,692,156, 4,804,370, 4813,936 and 4,931,040 which are illustrative of such protective syringes.

Although most of these devices provide means for safely protecting the ends of the needles, the cost of the syringe is relatively high. Moreover, many of these devices are useful only with syringes and do not afford any protection means for cannula used in other devices such as in cathertization and the like. Accordingly, it is an object of the present invention to provide a novel means for protecting such cannula from accidental contact with a user. It is another object of the invention to provide protective means for cannula which are both effective and relatively inexpensive to produce.

SUMMARY OF THE INVENTION

Generally, the present invention provides a flexible, sterilizable protective sheath member, preferably of a plastic, elastomeric silicone rubber polymer, slidably disposed over the cannula. In a preferred embodiment of the invention, a thin, hard, plastic tubular member is disposed over the cannula and extends in a preset arcuate form beyond the distal end of the cannula. In this embodiment, at least one pair of parallel, spaced apart slits are positioned in the protective tubular member or sheath. The slits facilitate movement of the protective sheath away from the distal end of the cannula and form elongated folded strips in its collapsed position prior to insertion of the cannula into the body.

In this preferred embodiment, small hooks may be formed in the distal arcuate end of the protective sheath. These hooks facilitate gripping by the end of the tubular member onto a portion of the periphery of the opening formed by the cannula. When the cannula is removed from the body, the hooks grab or provide a resistance so as to pull the protective sheath over the distal end of the cannula from a compressed position when the cannula is inserted in the body. The elongated, folded strips also unfold as the protective sheath moves over the distal end of the cannula, upon its withdrawal from the body.

In another embodiment of the invention, the sheath is utilized with a cannula-catheter device to protect the tip of the cannula after its insertion and removal from the body. Preferably, the sheath is a thin, hard, plastic tube. It is interposed between the cannula and catheter. However, rather than being "pulled out" by the tissues, as in the previous embodiment, the sheath is pulled over the cannula by the act of inserting the catheter. No hooks need be incorporated in the sheath as it is the friction of the catheter against the surface of the sheath which acts to move the sheath. The arcuate distal end of the sheath protects the cannula tip as with the previous embodiment.

In yet another embodiment of the invention, the protective sheath is made of an elastic thick-walled rubbery or silicone rubber polymer. The sheath extends in an arcuate form beyond the distal end of the cannula. In this embodiment, however, the initial position of the sheath is extended over the distal end, as compared with the previously described embodiments where the sheaths are initially located in a retracted position prior to cannula insertion. In this embodiment, it is necessary for the user to "lift" the arcuate end so as to expose the cannula tip prior to its insertion into the body. This lifting is done by pushing the arcuate end laterally against the subject tissues just prior to inserting the cannula. This is simple to do because the sheath is partially cut to expose a sufficient portion of the inner lumen of the tube on bending the tip. Upon insertion of the cannula, the protective sheath is compressed proximally toward the hub of the cannula, as the arcuate tip is bent aside. The slits facilitate this compression. Upon withdrawal of the cannula from the body, the protective sheath decompresses and moves toward the distal end such that the arcuate tip extends over and covers the cannula point to protect against accidental contact. The curved sheath tip flips back and thereby protects the straight cannula. In variations of this embodiment, the proximate end of the sheath can be preformed in spring-like configurations to assist in straightening the sheath to positively assure that the sheath end covers the distal end of the cannula upon removal from the body. In this last embodiment, it should be noted that the retractable sheath must have some inherent elasticity or springiness as this is required to push the sheath back over the tip on removal of the cannula from the body. The elasticity of the material also returns the sheath tip to its preset position, protecting the cannula tip upon its removal from the body. The other two embodiments are designed to be pulled over the cannula tip rather than being pushed out by elastic forces.

The protective sheath of the present invention provides a safe, positive and inexpensive means for protecting users of hyperdermic needles, syringes, catheters and like medical devices from accidental contact with a used cannula. Other advantages of the present invention will become apparent from a perusal of the following detailed description of presently preferred embodiments taken together with the following drawings.

DESCRIPTION OF PRESENTLY PREFERRED EMBODIMENTS

Figure 1:
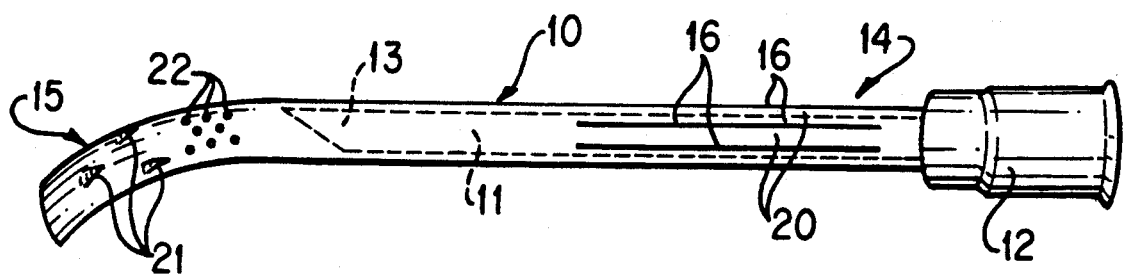
FIG. 1 is a side elevation of the protective sheath over the cannula.
Figure 2:
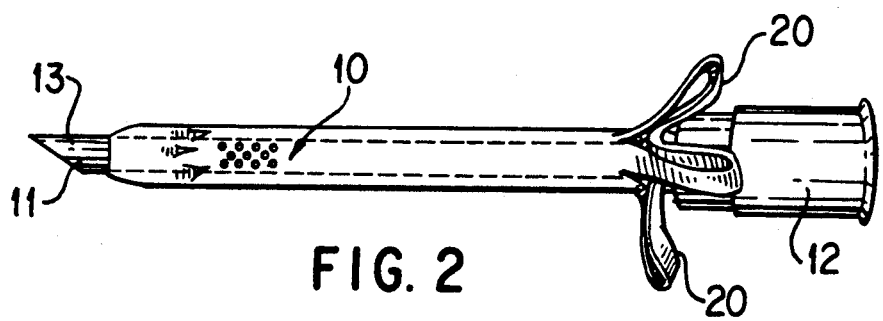
FIG. 2 is a side elevation of the protective sheath shown in FIG. 1 in its retracted position.

With reference to FIGS. 1 and 2 a protective sheath 10 comprising a thin-walled tubular member, preferably of a plastic material, is shown over cannula 11 and attached to cannula hub 12. Cannula 11 includes a sharp pointed distal end 13 for percutaneous insertion into a body. Protective sheath 10 includes an arcuate portion at the distal end 15 of the tubular member which extends beyond distal end 13 of cannula 11. Provided along a length of sheath 10 near the proximate end 14 thereof are a plurality of elongated, spaced apart slits 16. Because the protective sheath tubular member in this embodiment is quite thin in the wall section, the sheath can be used with a catheter.

Preferably, at least two slits 16 are used; although two or three pairs of slits in which the pairs are equidistantly located about the circumference of the tubular member may be advantageously used. However, it should be recognized that one pair of slits 16 will permit the two halves of member to compress away from distal end 13 upon compression. Slits 16, therefore, preferably define a plurality of elongated strips 20 which are adapted to move out of the plane of the tubular member upon movement of distal end 15 towards hub 12. This is better shown in FIG. 2 where strips 20 are folded against hub 12 upon movement of the distal end of sheath 10 over distal end 13 of cannula 11 during percutaneous use thereof.

In this embodiment, sheath 10 is compressed prior to insertion of the cannula into the body tissue. This may be done by simply sliding the tubular member towards hub 12 prior to use.

Preferably, distal end 15 of sheath 10 includes a plurality of small projective hooks 21. Also shown are small openings 22. Hooks 21 and openings 22 are useful for engaging the periphery of the opening formed by the percutaneous insertion of the cannula into the body. By engagement with the periphery, a gripping or resistive force is provided between the opening periphery and the sheath to inhibit movement of the sheath as the cannula is removed. It is thus possible for the sheath to be restored to its original shape by pulling it from the configuration shown in FIG. 2 back to the original shape shown in FIG. 1 by using the hystersis memory of the plastic material. FIG. 2 shows this embodiment its position of initial function, whereas FIG. 1 shows its final position protecting the cannula tip. Where the sheath is interposed between a cannula and catheter, the act of inserting the catheter and removing the cannula will result in moving the sheath over the distal end of the cannula.

Preferably, protective sheath 10 is made from a very thin polypropylene material or other thin, hard plastic polymer. The sheath is preferably approximately three to ten mills in thickness and arcuate portion at distal end 15 is heat set or extruded in the arcuate form so as to provide a hysteresis which permits the end to reassume its arcuate form upon removal of the cannula from the body. Slits 16 are machine or laser cut to provide precise, but inexpensive cuts or slots.

Figure 3:
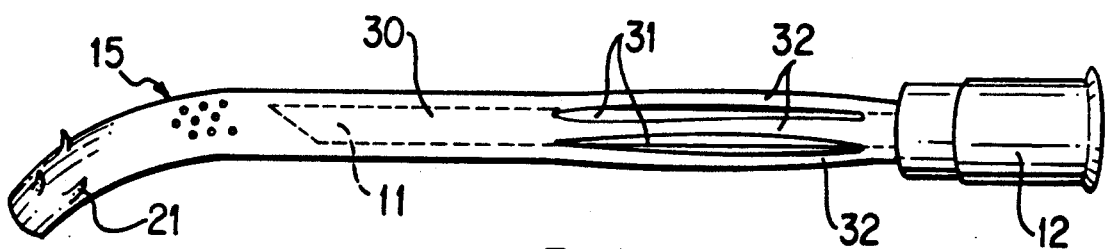
FIG. 3 is another embodiment of the protective sheath shown in FIG. 1 having preformed slots in the proximate end thereof.
Figure 4:
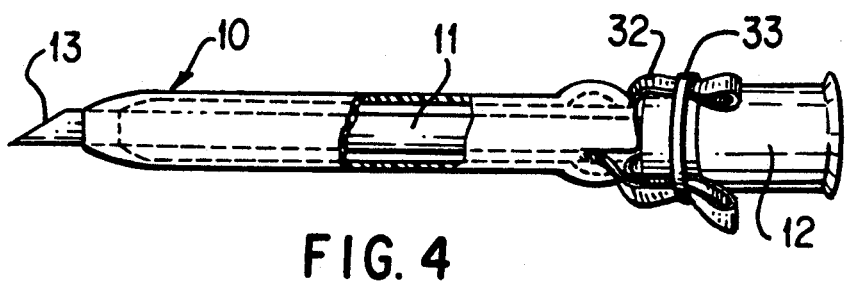
FIG. 4 is another embodiment of the protective sheath shown in FIG. 1 in its retracted position with a band positioned about the extended, folded strips to retain the sheath in the retracted position.

Referring to FIG. 3, another embodiment of protective sheath is shown. In this embodiment, protective sheath 30 comprising a tubular member includes a plurality of elongated, elliptical openings 31 which define strips 32 positioned therebetween. Protective sheath 30 is preferably made from a very thin plastic material as described above. Utilizing elliptical openings 31 facilitates retraction and compression of sheath 30 over cannula 11. The embodiment shown in FIG. 4 is particularly useful with cannulas where the cannula 11 remains in he body for an extended period of time. As shown in FIG. 4, a small band 33 can be placed on folded strips 32 to maintain sheath 30 in the retracted position. Upon removal of the cannula from the body, band 33 is removed to allow the protective sheath 30 to move and thereby protect the cannula tip.

Figure 5:
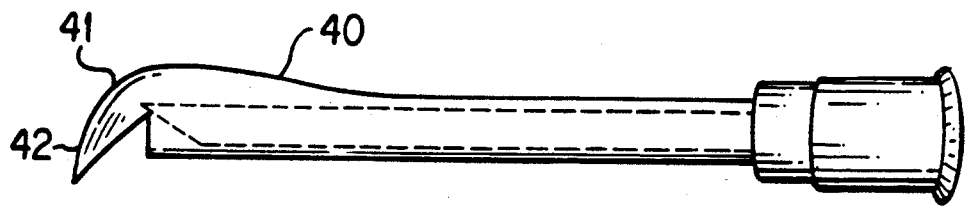
FIG. 5 is another embodiment of the protective sheath of the present invention having a tip formed at its distal end.
Figure 8:
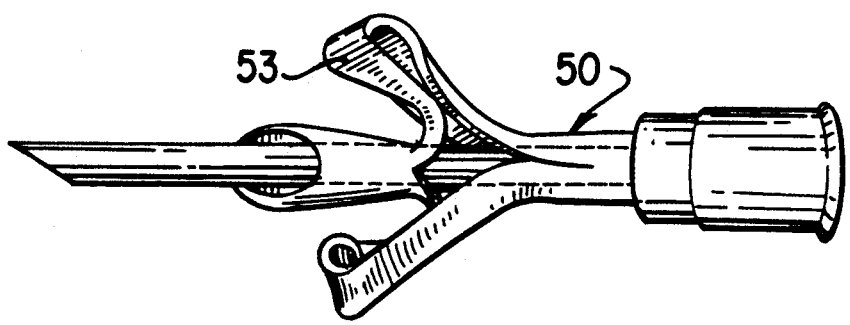
FIG. 8 is a side elevation of the protective sheath, shown in FIG. 5, in its retracted position.

Referring to FIG. 5, another embodiment of the protective sheath of the present invention is shown. In this embodiment, protective sheath 40 comprising a tubular member which includes at its distal end 41 a cover or tip 42 which depends over and covers distal end 13 of cannula 11. Upon insertion of cannula 11 into a body, tip 42 is lifted by the user over the distal portion of the needle and pulled back slightly from the distal end of the cannula during its insertion into the body. Compression of sheath 40 can be seen in FIG. 8 and 12 where the proximate end is compressed.

Preferably, protective sheath 40 is made from a rubber material that is sterilizable, such as silicone rubber or neoprene. In this embodiment, the thickness of the tubular wall material is not as important. That is, sheath 40 can be quite a bit thicker than the previously described embodiment. A slightly thicker wall section, e.g., 10-20 nils, facilitates restoration of shape after compression and use of the cannula.

Figure 6:
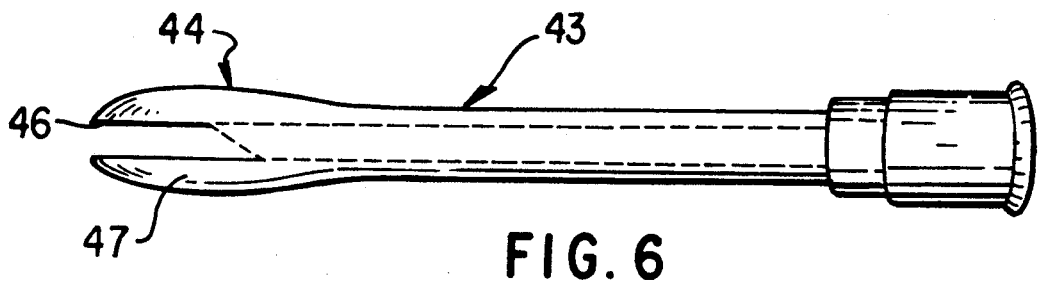
FIG. 6 is a variation of the sheath shown in FIG. 5 having a cut and flared distal end.

Referring to FIG. 6, protective sheath 43 includes at its distal end 44 a pair of extended tips 46 and 47. In this embodiment, tips 46 and 47 separate or spread apart upon insertion of cannula 11 into the body as cannula 11 is inserted sheath 43 retracts out of the way. This embodiment has the advantage of providing secondary protection against accidental contact with the cannula point, but is easy to use. Since tips 46 and 47 spread apart as the cannula moves toward the user, the user does not have to use any additional manipulation.

Figure 7:
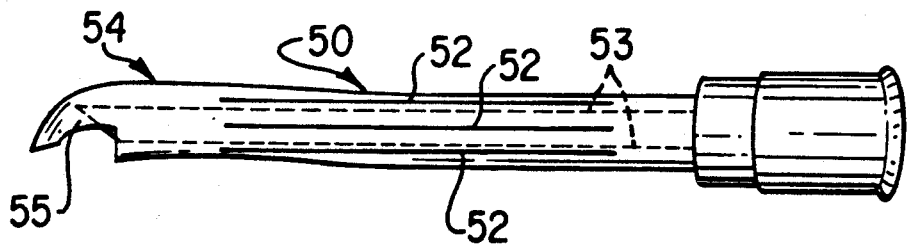
FIG. 7 is a side elevation of a sheath shown in FIG. 5 having a plurality of slits formed therein as shown with respect to the embodiment described with respect to FIG. 3.

In a presently preferred embodiment of the invention, a protective sheath similar to that shown and described with respect to FIG. 5 is provided with a plurality of slots. This is shown in FIG. 7 where protective sheath 50 comprising a tubular member such as tubular neoprene, silicone rubber or other elastomeric medical rubber tubing or plastic tubing. It is provided with a plurality of elongated slits 52 which define therebetween foldable strips 53. At its distal end 54, protective sheath 50 includes tip member 55. Upon insertion of the cannula 11 into the body or vessel, slits 52 permit retraction of sheath 50 so that strips 53 fold out of the plane of sheath 50. This is better seen with respect to FIG. 8 in which sheath 50 has been retracted towards the proximate end of the cannula, similar to the embodiment described with respect to FIG. 1.

Figure 9:
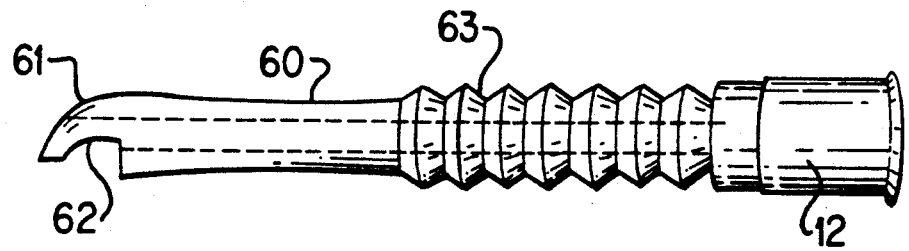
FIG. 9 is a side elevation of a protective sheath shown in FIG. 5 having preformed spring means.
Figure 10:
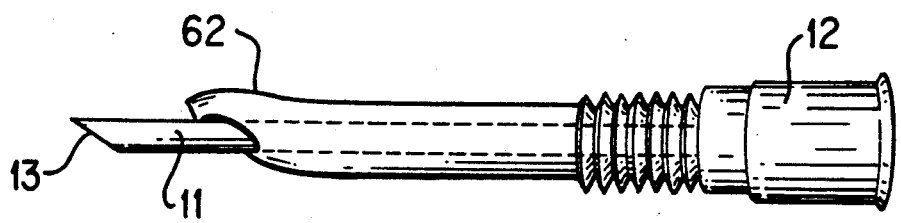
FIG. 10 is a side elevation of protective sheath shown in FIG. 9 in retracted position.

Referring to FIGS. 9 and 10, sheath 60 comprising a tubular member is formed with tip member 62 which depends over and covers at its distal end 61 the point of cannula 11. Pre-formed, for example by heat treatment and compression, at the proximate end of sheath 60 are a plurality of bellow-like ridges 63. Ridges 63 facilitate compression of sheath 60, as shown in FIG. 10, during insertion of cannula 11 into the skin. More importantly, however, compressed ridges 63 afford positive restoration of the sheath over the end of the cannula.

Figure 11:
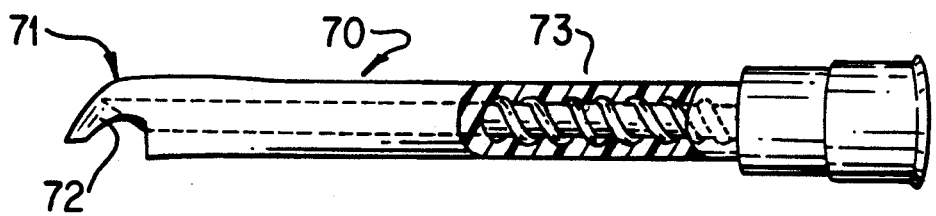
FIG. 11 is another embodiment of the protective sheath shown in FIG. 5 having an internal spring member positioned over the cannula and engaging the inner surface of the sheath.

With reference to FIG. 11, sheath 70 includes a depending tip member 72 at distal end 71. Positioned at the proximate end of sheath 70 is spring member 73. As shown, spring member 73 is a compression coil spring positioned against the inner surface of sheath 70. However, other types of springs can be used such as a small leaf spring positioned between the cannula nd inner surface of sheath 70 as well as torsion springs. The use of spring member 73 provides a positive force to decompress the sheath when retracted for cannula insertion.

Figure 12:
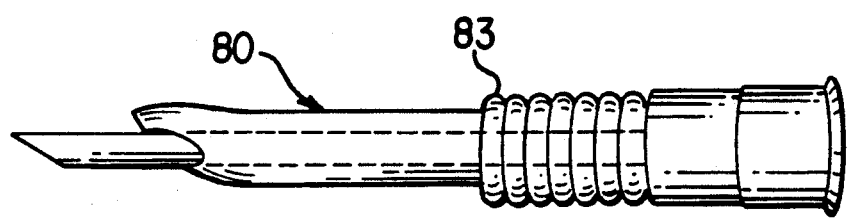
FIG. 12 is a side elevation of the protective sheath in retracted position using preformed ridges to provide spring-like decompression.

With respect to FIG. 12, a further embodiment of the sheath show with respect to FIG. 9. In this embodiment, sheath 80 is shown in retracted position with a bellow-like preformed member 83 compressed. As can be seen from the embodiments of FIGS. 9 and 12, methods for facilitating the compression of the sheath varied.

Figure 13:
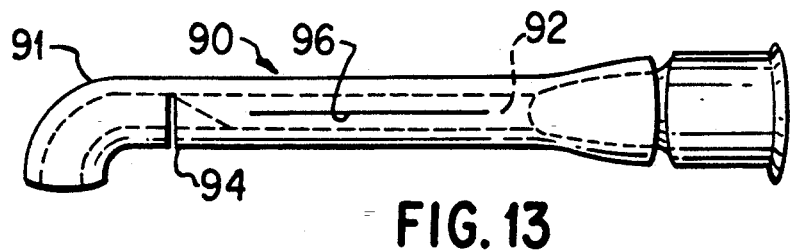
FIG. 13 and 17 are side elevations of the protective sheath wherein the arcuate distal portion is arched over the distal end of the cannula.

As shown in FIG. 13, protective sheath 90 is positioned over a cannula 92 and includes an arcuate position 91 at its distal end. Arcuate position 91 extends beyond the distal end of cannula 92 and includes radial slit 94. Radial slit 94 extends into the protective sheath to facilitate removal of distal portion 91 from the point of cannula 92 during use. Sheath 90 also includes elongated slit 46 to permit formation of foldable strips 97.

Figure 14:
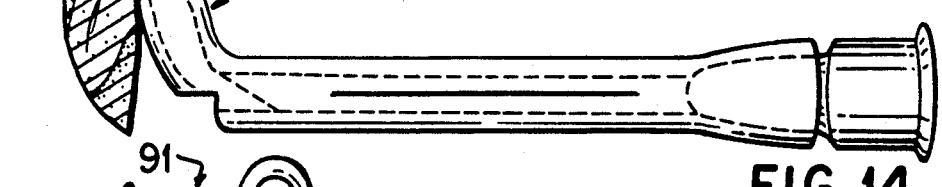
FIGS. 14-16 are side elevation of the sheath shown in FIG. 13 in various positions of compression and decompression.
Figure 15:
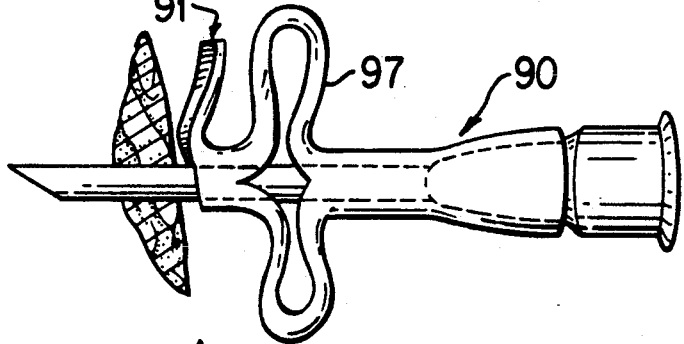
Figure 16:
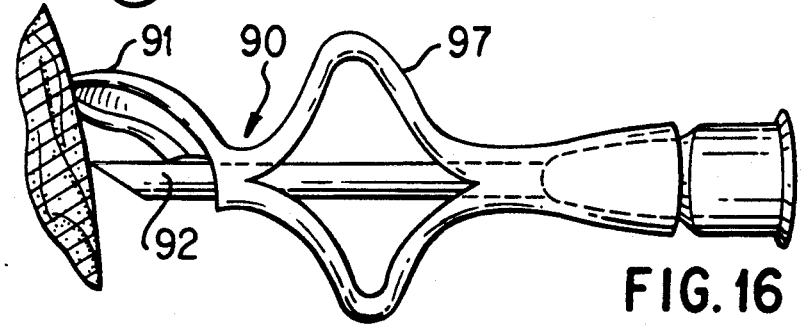

Referring to FIGS. 14-16, the use of protective sheath 90 is graphically illustrated. In FIG. 14, distal portion 91 is moved out of the way by pressing it against the skin. Upon insertion into the skin, sheath 90 compresses over cannula 92 toward the proximate end, FIG. 15. FIG. 16 depicts the restoration of sheath 90 upon withdrawing the cannula.

Figure 17:
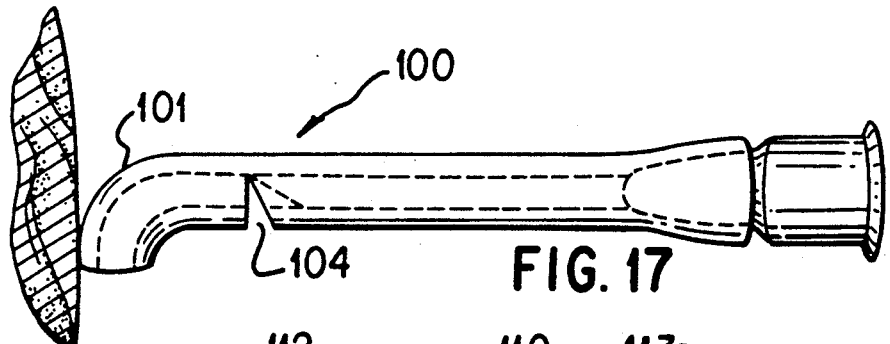

Referring to FIG. 17, sheath 100 is shown which is substantially the same as sheath 90, described in reference to FIG. 13. In this embodiment a triangular radio station is used to facilitate movement of arcuate distal portion 101.

Figure 18:
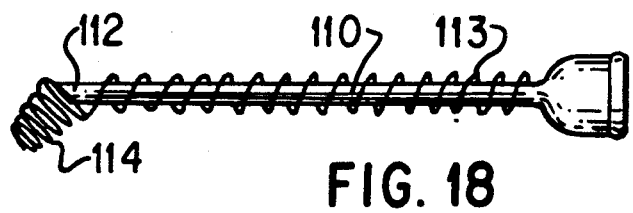
FIG. 18 is another embodiment utilizing spring members as the tubular member.

Referring to FIG. 18, another embodiment utilizing a compression spring 13 over cannula 110. Compression spring 113 includes depending distal end 114 over distal portion 112 of cannula 110. Preferably, distal portion 114 comprises a torsion spring to prevent cannula end 112 from extending through the abutting convolutions. Also, it is preferable that spring 113 include a coating.

Accordingly, while presently preferred embodiments of the invention have been shown and described in particularity. The invention may be otherwise embodied within the scope of the amended claims.

What is claimed:

1. A protective sheath for a cannula having a distal end for percutaneous insertion, said protective sheath comprising an elongated, flexible tubular member for slidably fitting over said cannula, said tubular member having a distal end arcuately depending over the distal end of said cannula and compressibly retractable therefrom and a proximate end, said distal end having an opening through which the cannula may pass whereby the distal end of the cannula is exposed during insertion thereof, and the distal end of the sheath extends over and covers the distal end of the cannula when the cannula is withdrawn.

2. A protective sheath as set forth in claim 1 wherein said arcuate distal end of said tubular member includes a slit adjacent the distal end of said cannula such that said end opens off axis of said cannula.

3. A protective sheath as set forth in claim 1 wherein said arcuate distal end comprises a tip member depending over said distal end of said cannula and includes a slit to permit opening off axis.

4. A protective sheath as set forth in claim 1, 2, or 3 wherein said tubular member includes at least one pair of elongated, spaced apart slits which define at least two foldable strips, said slots being located away from said distal end of said sheath.

5. A protective sheath as set forth in claim 1 wherein said distal end of said tubular member includes a plurality of protrusions.

6. A protective sheath as set forth in claim 1 or 5 in which said distal end of said sheath includes a plurality of openings therein.

7. A protective sheath as set forth in claim 3 wherein said tubular member is formed in the shape of a bellow at its proximate end to enhance decompression of said sheath.

8. A protective sheath as set forth in claim 3 including a spring member positioned between said cannula and tubular member at its proximate end.

9. A protective sheath as claimed claim 1 or 2 wherein said tubular member comprises a spring.

10. A protective sheath as claimed in claim 9 wherein said spring is a compression spring.

11. A protective sheath as claimed in claim 1 or 2 wherein said tubular member comprises a first compression spring and a second torsion spring comprising the distal end of said sheath.

12. A protective sheath as set forth in claim 1, 2 or 3, 4 wherein said tubular member is molded.

* * * * *